(12) United States Patent
Choudhary et al.

(10) Patent No.: US 12,310,980 B2
(45) Date of Patent: May 27, 2025

(54) SYNTHESIS OF A POTENT AROMATASE INHIBITOR 17α-ACETOXY-10β,11β-DIHYDROXY-PROGESTERONE FOR THE TREATMENT OF ER+ BREAST CANCER

(71) Applicants: Muhammad Iqbal Choudhary, Karachi (PK); Atia-tul-Wahab, Karachi (PK); Humaira Zafar, Karachi (PK); Ambreen Aziz, Karachi (PK); Nimra Naveed Shaikh, Karachi (PK); Atta-ur-Rahman, Karachi (PK)

(72) Inventors: Muhammad Iqbal Choudhary, Karachi (PK); Atia-tul-Wahab, Karachi (PK); Humaira Zafar, Karachi (PK); Ambreen Aziz, Karachi (PK); Nimra Naveed Shaikh, Karachi (PK); Atta-ur-Rahman, Karachi (PK)

( * ) Notice: Subject to any disclaimer, the term of this patent is extended or adjusted under 35 U.S.C. 154(b) by 98 days.

(21) Appl. No.: 18/128,246

(22) Filed: Mar. 30, 2023

(65) Prior Publication Data

US 2023/0241079 A1 Aug. 3, 2023

(51) Int. Cl.
*A61K 31/57* (2006.01)
*A61P 35/00* (2006.01)

(52) U.S. Cl.
CPC ............. *A61K 31/57* (2013.01); *A61P 35/00* (2018.01)

(58) Field of Classification Search
CPC ...................................... A61K 31/57
See application file for complete search history.

(56) References Cited

U.S. PATENT DOCUMENTS

2021/0230214 A1* 7/2021 Choudhary ............. A61P 35/00

* cited by examiner

*Primary Examiner* — Kortney L. Klinkel
*Assistant Examiner* — Donna M Nestor

(57) ABSTRACT

Biotransformation of gestonorone acetate (1) with *Cunninghamella blakesleeana* (ATCC 8688) yielded a new analogue, 17α-actoxy-10β,11β-dihydroxy-progesterone (2). Compound 2 was identified as non-cytotoxic inhibitor of human aromatase enzyme ($IC_{50}=0.827\pm0.066$ μM). Compound 2 showed a significant aromatase inhibitory activity, as compared to the standard aromatase inhibitory drug, exemestane ($IC_{50}=0.232\pm0.03$ μM).

2 Claims, 1 Drawing Sheet

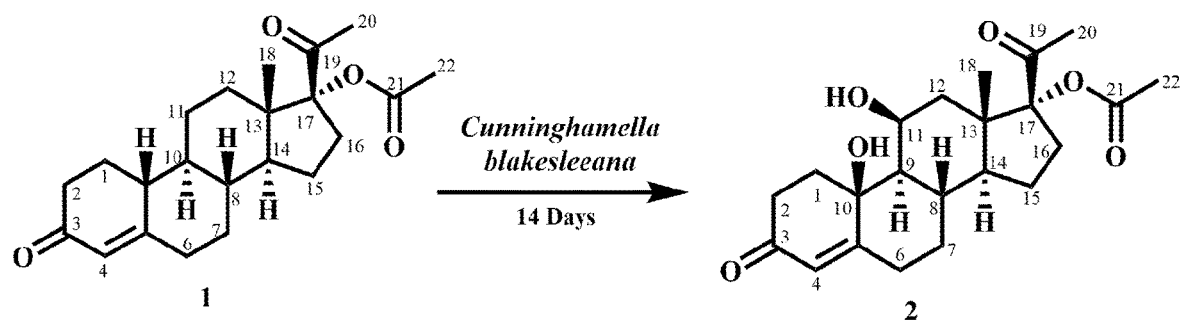

SYNTHESIS OF A POTENT AROMATASE INHIBITOR 17α-ACETOXY-10β,11β-DIHYDROXY-PROGESTERONE FOR THE TREATMENT OF ER+ BREAST CANCER

BACKGROUND OF THE INVENTION

Gestonorone acetate (1) ($C_{22}H_{30}O_4$) (m/z 358.4) 47 (17α-acetoxy-19-nor-progesterone), also known as norhydroxyprogesterone acetate, is used as a precursor of several biologically active compounds. It is reported to inhibit ovulation at a oral dosage of 10 mg/day in combination with 50 μg/day ethinylestradiol.

Breast cancer is the most prevalent cancer in women globally and is the major cause of cancer related mortality among females. Most of the diagnosed breast cancer are hormone dependent that are developed due to the overproduction of estrogen and are termed as estrogen dependent or ER+ breast cancers. Aromatase enzyme is responsible for the catalytic production of estrogen (estrone and estradiol) from androgens (androstenedione and testosterone) in the human body. It has been established that inhibiting aromatase have significant effects in breast cancer cells and it is therefore, considered as therapeutic target for the treatment of hormone dependent breast cancers. Aromatase inhibitors (AIs) are used post-surgical interventions to maintain the estrogen level and thereby decreasing the risk of recurrence of the disease. Currently used AIs include steroidal analogues (exemestane), and non-steroidal inhibitors (anastrazole, and letrozole). Several side effects are associated with currently available drugs including, hot flashes, headache, and vaginal dryness. Some aromatase inhibitors have also been reported to increase the osteopenia, osteoporosis, musculoskeletal symptoms, and fractures. Therefore, there is a need to develop new aromatase inhibitors with better oral bioavailability, and fewer side effects.

Biotransformation is an excellent green chemistry approach for the derivatization of bioactive compounds, because of its low cost, scalability, and environment friendly procedures. Biocatalytic reactions yields stereo-, regio-, and chemo-selective products by using fungal or bacterial cultures. Biotransformation of parent compound results into the products which have batter activity profile or the products with new activity. Fungal whole cell culture can catalyze different reactions such as reduction, oxidation, hydrolysis, isomerization, introduction of new functionality by using their unique enzymatic system named P450 monooxygenase.

BRIEF SUMMARY OF THE INVENTION

In continuation of our research on microbial transformations, gestonorone acetate (1) was incubated with *Cunninghamella blakesleeana* at ambient reaction conditions. This yielded a new metabolite, 17α-acetoxy-10β,11β-dihydroxy-progesterone (2) characterize by using modern spectroscopic techniques.

Gestonorone acetate (1) and its metabolites 2 was evaluated for human aromatase inhibitory potential. Substrate 1 ($IC_{50}$=0.7405±0.0241 μM) and its derivative 2 ($IC_{50}$=0.827±0.066) showed a significant aromatase inhibition, as compared to the standard AI drug exemestane ($IC_{50}$=0.232±0.03 μM) in vitro.

BRIEF DESCRIPTION OF THE DRAWINGS

FIG. 1 depicts the structures of gestonorone acetate (1), and its new metabolites 2, via *Cunninghamella blakesleeana*-mediated transformation of compound 1, along with their aromatase inhibitory activity.

DETAILED DESCRIPTION OF THE INVENTION

Microorganism and Culture Conditions

Fungal cultures of *C. blakesleeana* (ATCC 8688a) was grown on Sabouraud dextrose agar at 25° C., and stored at 4° C. The composition of 1.0 L media for the growth of *C. blakesleeana* include glucose (10.0 g), glycerol (10.0 mL), peptone (5.0 g), yeast extract (5.0 g), $KH_2PO_4$ (5.0 g), and NaCl (10.0 g) mixed into distilled $H_2O$ (1.0 L). Using the mentioned protocol 2.2 L media was prepared, autoclaved, and then distributed to 22 conical flasks (100 mL media each). Each flask was inoculated with the culture of *C. blakesleeana* and incubated at room temperature on shaker at 1400 rpm for four days.

Fermentation of Gestonorone Acetate (1) with *Cunninghamella Blakesleeana* (ATCC 8688)

Compound 1 (2.0 g/100 mL acetone) was then distributed among 22 flasks containing 4-day-old culture of *C. blakesleeana* and kept for fermentation for 14 days. The reaction was stopped by adding 80 mL ethyl acetate in each flask. The media was then filtered and extracted with ethyl acetate (three times). The crude organic layer was then separated and evaporated under vacuum to obtained brown gummy material (8.2 g). The crude gummy material was subjected to column chromatography over silica gel (70-230 mesh) and eluted with increasing polarity of acetone in petroleum ether. The obtained fractioned were pooled using thin layer chromatography (silica gel, 20×20, 0.25 mm thick). Main fraction (Ges-1) was further subjected to recycling reverse phase HPLC (JAI LC-908W), equipped with YMC-L-80) 4-5 μM, 20-50 mm i.d.) for final purification. Fraction (Ges-1) afforded pure compounds 2 (retention time 25 min, $CH_3OH$: $H_2O$; 60:40).

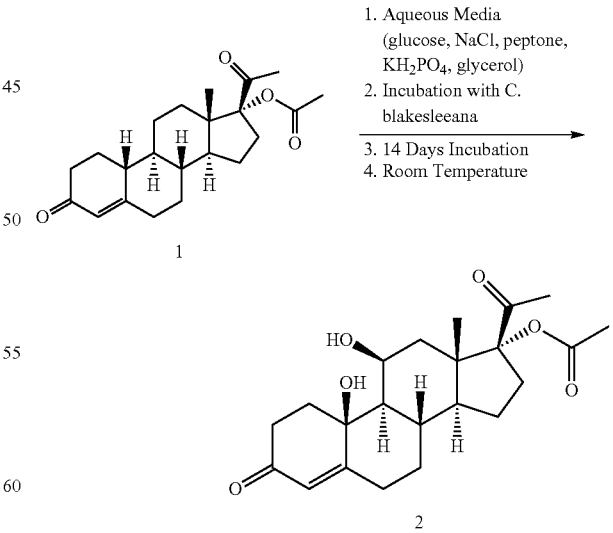

17α-Acetoxy-10β,11β-dihydroxy-progesterone (2)

White solid (800 mg); $[\alpha]_D^{25}$: +21.8 (c=0.01, MeOH); UV (MeOH): $\lambda_{max}$ nm: 243, and 247; IR (KBr); $v_{max}$ $cm^{-1}$: 3512 (OH), 2950 (CH), 1619 (ester); $^1$H-NMR ($CD_3OD$, 600 MHz), $H_2$-1 (2.65, m; 2.11, m), $H_2$-2 (2.32, overlapped), H-4 (5.75, br.s), H-6 (2.74, td; 2.31, overlapped), $H_2$-7 (1.99, m; 1.15, m), H-8 (2.22, m), H-9 (1.28, dd), H-9 (4.64, br. d), $H_2$-12 (2.18, m; 1.77, m), H-14 (1.80, m), $H_2$-15 (1.76, m; 1.41, m), $H_2$-16 (2.89, m; 1.73 m), $H_3$-18 (0.90, s), $H_3$-20 (2.03, s), $H_3$-22 (2.05, s); $^{13}$C-NMR (CD$_3$OD, 150 MHz):): C-1 (34.4), C-2 (34.8), C-3 (202), C-4 (125.0), C-5 (166.5), C-6 (32.5), C-7 (32.9), C-8 (32.5), C-9 (54.7), C-10 (72.5), C-11 (69.7), C-12 (39.7), C-13 (47.4), C-14 (52.6), C-15 (24.7), C-16 (31.1), C-17 (97.6), C-18 (17.2), C-19 (206.0), C-20 (26.8), C-21 (172.5), C-22 (21.0); FAB-MS m/z [M-H]$^+$: 391 HRFAB-MS m/z 391.1265 (mol. formula $C_{22}H_{31}O_6$, calcd 391.1263).

Assay Protocol for Aromatase Inhibition

UPLC-based aromatase inhibition assay was performed to determine the enzyme inhibition potential of the biotransformed product. The activity was determined in 1 mL volume reaction, containing protein (2 mg) from human placental microsomes, and 10 µL testosterone (10 PM) in methanol and 0.1 mM of test sample in methanol, pre-incubated at 37° C. for 10 minutes. NADPH (1 mM) was added to initiate the reaction, containing potassium phosphate (0.1 M; pH 7.4), and incubated for 20 minutes. Reaction was terminated by adding 100 µL of trichloroacetic acid (10%, w/v), followed by centrifugation at 12,000 g for 10 minutes, resulting pellet was discarded. 17β-estradiol was extracted with n-butyl chloride (1 mL) from the supernatant, and the sample was dried. Amount of 17β-estradiol in the supernatant was determined through UPLC, using triethylamine (0.1%) in ACN/H$_2$O (45:55, v/v) as a mobile phase at pH of 3.0. The pH was adjusted by adding ortho-phosphoric acid. Isocratic elution at flow rate of 1.2 mL/min was carried out at 200 nm.

Calculations were performed by following formula:

% Enzyme Inhibition=100−(Peak area of test sample)/(Peak area of control)×100

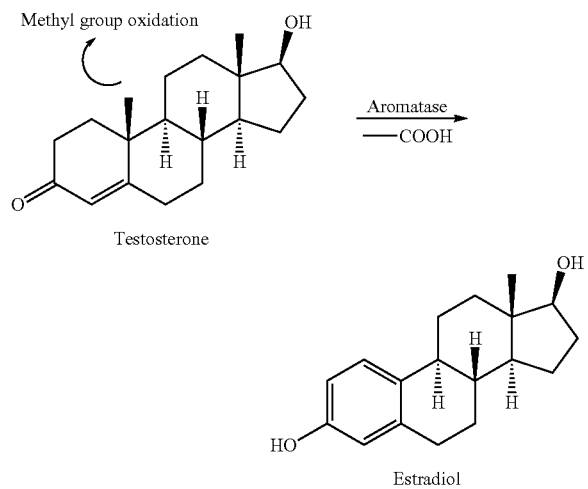

Results and Discussion

Biotransformation of gestonorone acetate (1) was carried out with *Cunninghamella blakesleeana* (ATCC 8688). This yielded a new metabolite, 17α-acetoxy-10β,11β-dihydroxy-progesterone (2).

The HRFAB-MS of metabolite 2 showed its [M-H]$^{+\cdot}$ at m/z 391.1265 (mol. formula $C_{22}H_{31}O_6$, calcd. 391.1263), suggesting addition of two oxygen atoms. The IR spectrum of derivative 2 also showed broad absorption at 3512 cm$^{-1}$ for hydroxyl groups. The dihydroxylation in compound 2 was further determined from 1D-, and 2D-NMR spectral data.

In conclusion, transformation of gestonorone acetate (1) with *Cunninghamella blaksleena* led to the synthesis of a new dehydroxylated metabolite 2. Derivative 2 showed a significant aromatase inhibitory activity with the IC$_{50}$ value of 0.827±0.066 µM and found to be non-cytotoxic against human fibroblast cell line.

What is claimed is:

1. A gestonorone acetate derivative, 17α-acetoxy-10β, 11β-dihydroxy-progesterone, having the following chemical structure:

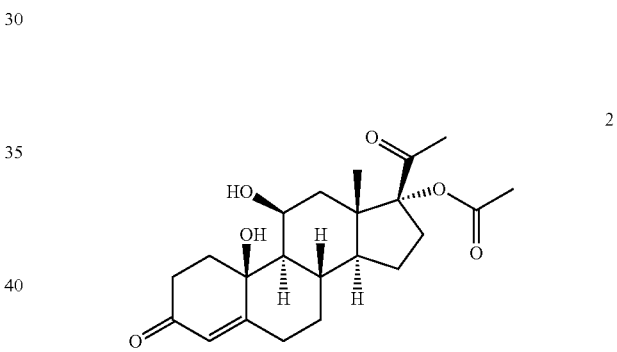

or a pharmaceutically acceptable salt thereof.

2. A method of treatment of estrogen-responsive (ER+) breast cancer, the method comprising administering an effective amount of the compound of claim 1 or a salt thereof in a pharmaceutical excipient, adjuvant, carrier or diluent to a human in need thereof.

* * * * *